(12) United States Patent
Uhlmann (10) Patent No.: US 11,541,161 B2
(45) Date of Patent: Jan. 3, 2023

(54) SYSTEM AND METHOD FOR CONTINUOUS FLOW RED BLOOD CELL WASHING

(71) Applicant: Haemonetics Corporation, Boston, MA (US)

(72) Inventor: Dominique Uhlmann, Abington, MA (US)

(73) Assignee: Haemonetics Corporation, Boston, MA (US)

( * ) Notice: Subject to any disclaimer, the term of this patent is extended or adjusted under 35 U.S.C. 154(b) by 868 days.

(21) Appl. No.: 16/311,455

(22) PCT Filed: Jun. 22, 2017

(86) PCT No.: PCT/US2017/038761
§ 371 (c)(1),
(2) Date: Dec. 19, 2018

(87) PCT Pub. No.: WO2017/223318
PCT Pub. Date: Dec. 28, 2017

(65) Prior Publication Data
US 2019/0231964 A1    Aug. 1, 2019

Related U.S. Application Data

(60) Provisional application No. 62/354,162, filed on Jun. 24, 2016.

(51) Int. Cl.
*A61M 1/36* (2006.01)

(52) U.S. Cl.
CPC ........ *A61M 1/3692* (2014.02); *A61M 1/3693* (2013.01); *A61M 1/3696* (2014.02);
(Continued)

(58) Field of Classification Search
CPC .............. A61M 1/3692; A61M 1/3693; A61M 1/3696; A61M 2205/3306;
(Continued)

(56) References Cited

U.S. PATENT DOCUMENTS

| 3,645,252 A | 2/1972 | Gilford |
| 3,655,123 A | 4/1972 | Judson et al. |

(Continued)

FOREIGN PATENT DOCUMENTS

| CA | 2840901 A1 | 1/2013 |
| EP | 0223126 A2 | 5/1987 |

(Continued)

OTHER PUBLICATIONS

Ferraris et al., Perioperative blood transfusion and blood conservation in cardiac surgery: the Society of Thoracic Surgeons and the Society of Cardiovascular Anesthesiologists clinical practice guideline. Ann Thorac Surg. May 2007;83(5 Suppl):S27-86.

(Continued)

*Primary Examiner* — Ariana Zimbouski
(74) *Attorney, Agent, or Firm* — McCarter & English, LLP; Jonathan C. Lovely (57) ABSTRACT

A method for continuously washing packed red blood cells includes (1) transferring, at a first flow rate, packed red blood cells from a container to a separation device and (2) transferring, at the same time as the packed red blood cells, wash solution from a container to the separation device. The wash solution may be transferred at a second flow rate that is greater than the first flow rate. The wash solution mixes with the packed red blood cells within the inlet line of the separation device and dilutes/washes the packed red blood cells. The separation device separates the red blood cells from the wash solution and a supernatant. The method may then monitor the volume of washed red blood cells within the separation device and begin to extract the washed red blood cells into a red blood cell product container when a target volume is collected within the separation device.

41 Claims, 8 Drawing Sheets

(52) U.S. Cl.
CPC .............. *A61M 2202/0429* (2013.01); *A61M 2205/3306* (2013.01); *A61M 2205/3393* (2013.01)

(58) Field of Classification Search
CPC ........... A61M 2205/3393; B04B 11/04; B04B 13/00; B04B 5/0442
See application file for complete search history.

(56) References Cited

U.S. PATENT DOCUMENTS

| | | | |
|---|---|---|---|
| 3,768,653 | A | 10/1973 | Brumfield |
| 3,965,896 | A | 6/1976 | Swank |
| 4,033,345 | A | 7/1977 | Sorenson et al. |
| 4,049,192 | A | 9/1977 | Krebs et al. |
| 4,054,523 | A | 10/1977 | Ingenito et al. |
| 4,086,924 | A | 5/1978 | Latham, Jr. |
| 4,115,277 | A | 9/1978 | Swank |
| 4,151,844 | A | 5/1979 | Cullis et al. |
| 4,189,470 | A | 2/1980 | Rose |
| 4,236,960 | A | 12/1980 | Hultman et al. |
| 4,243,531 | A | 1/1981 | Crockett et al. |
| 4,321,192 | A | 3/1982 | Jain |
| 4,411,786 | A | 10/1983 | Russell |
| 4,416,654 | A | 11/1983 | Schoendorfer et al. |
| 4,482,342 | A | 11/1984 | Lueptow et al. |
| 4,531,954 | A | 7/1985 | Klein |
| 4,561,868 | A | 12/1985 | von Reis et al. |
| 4,668,214 | A | 5/1987 | Reeder |
| 4,673,423 | A | 6/1987 | Yumlu |
| 4,680,025 | A | 7/1987 | Kruger et al. |
| 4,681,677 | A | 7/1987 | Kuh et al. |
| 4,704,203 | A | 11/1987 | Reed |
| 4,743,371 | A | 5/1988 | Servas et al. |
| 4,758,337 | A | 7/1988 | Kohn et al. |
| 4,781,707 | A | 11/1988 | Boehringer et al. |
| 4,795,448 | A | 1/1989 | Stacey et al. |
| 4,806,252 | A | 2/1989 | Brown et al. |
| 4,828,543 | A | 5/1989 | Weiss et al. |
| 4,828,716 | A | 5/1989 | McEwen et al. |
| 4,834,890 | A | 5/1989 | Brown et al. |
| 4,872,988 | A | 10/1989 | Culkin |
| 4,886,487 | A | 12/1989 | Solem et al. |
| 4,898,572 | A | 2/1990 | Surugue nee Lasnier et al. |
| 4,919,817 | A | 4/1990 | Schoendorfer et al. |
| 4,943,273 | A | 7/1990 | Pages |
| 4,946,434 | A | 8/1990 | Plaisted et al. |
| 4,954,251 | A | 9/1990 | Barnes et al. |
| 5,015,388 | A | 5/1991 | Pusineri et al. |
| 5,055,198 | A | 10/1991 | Shettigar |
| 5,076,911 | A | 12/1991 | Brown et al. |
| 5,133,703 | A | 7/1992 | Boehringer et al. |
| 5,135,645 | A | 8/1992 | Sklenak et al. |
| 5,147,290 | A | 9/1992 | Jonsson |
| 5,182,019 | A | 1/1993 | Cote et al. |
| 5,183,569 | A | 2/1993 | Kyriacou |
| 5,215,519 | A | 6/1993 | Shettigar |
| 5,223,154 | A | 6/1993 | MacPherson, Jr. et al. |
| 5,234,403 | A | 8/1993 | Yoda et al. |
| 5,238,655 | A | 8/1993 | Laible et al. |
| 5,294,401 | A | 3/1994 | Hagiwara |
| 5,298,016 | A | 3/1994 | Gordon |
| 5,308,506 | A | 5/1994 | McEwen et al. |
| 5,311,908 | A | 5/1994 | Barone et al. |
| 5,344,570 | A | 9/1994 | McLachlan et al. |
| 5,378,227 | A | 1/1995 | O'Riordan et al. |
| 5,385,539 | A | 1/1995 | Maynard |
| 5,386,734 | A | 2/1995 | Pusinelli |
| 5,411,472 | A | 5/1995 | Steg, Jr. et al. |
| 5,411,705 | A | 5/1995 | Thor et al. |
| 5,417,650 | A | 5/1995 | Gordon |
| 5,419,759 | A | 5/1995 | Naficy |
| 5,423,738 | A | 6/1995 | Robinson et al. |
| 5,458,566 | A | 10/1995 | Herrig et al. |
| 5,464,399 | A | 11/1995 | Boettger |
| 5,478,479 | A | 12/1995 | Herrig |
| 5,554,293 | A | 9/1996 | Uhoch |
| 5,634,893 | A | 6/1997 | Rishton |
| 5,643,193 | A | 7/1997 | Papillon et al. |
| 5,651,766 | A | 7/1997 | Kingsley et al. |
| 5,658,256 | A | 8/1997 | Shields |
| 5,674,173 | A | 10/1997 | Hlavinka et al. |
| 5,725,777 | A | 3/1998 | Taylor |
| 5,733,253 | A | 3/1998 | Headley et al. |
| 5,770,073 | A | 6/1998 | Bach et al. |
| 5,800,721 | A | 9/1998 | McBride |
| 5,879,624 | A | 3/1999 | Boehringer et al. |
| 5,891,080 | A | 4/1999 | Skinkle et al. |
| 5,954,971 | A | 9/1999 | Pages et al. |
| 5,971,948 | A | 10/1999 | Pages et al. |
| 6,007,472 | A | 12/1999 | Schill et al. |
| 6,250,330 | B1 | 6/2001 | Welker |
| 6,251,284 | B1 | 6/2001 | Bischof et al. |
| 6,251,291 | B1 | 6/2001 | Lamphere et al. |
| 6,267,925 | B1* | 7/2001 | Pages ........................ A01N 1/02 210/739 |
| 6,464,624 | B2 | 10/2002 | Pages |
| 6,508,778 | B1 | 1/2003 | Verkaart et al. |
| 6,632,189 | B1 | 10/2003 | Fallen et al. |
| 6,632,191 | B1 | 10/2003 | Headley et al. |
| 6,723,086 | B2 | 4/2004 | Bassuk et al. |
| 6,800,072 | B2 | 10/2004 | Patzer |
| 6,890,316 | B2 | 5/2005 | Rawles et al. |
| 7,008,393 | B2 | 3/2006 | Robinson et al. |
| 7,037,428 | B1* | 5/2006 | Robinson ............. A61M 1/3693 210/360.1 |
| 8,016,736 | B2 | 9/2011 | Hlavinka et al. |
| 8,157,103 | B2 | 4/2012 | Eagle et al. |
| 8,409,125 | B2 | 4/2013 | Bobroff |
| 8,628,671 | B2 | 1/2014 | Eagle et al. |
| 10,293,097 | B2 | 5/2019 | Murphy et al. |
| 2005/0203469 | A1 | 9/2005 | Bobroff et al. |
| 2008/0058695 | A1 | 3/2008 | Perovitch et al. |
| 2008/0124700 | A1* | 5/2008 | Fortini .................... B04B 11/02 435/2 |
| 2013/0197470 | A1 | 8/2013 | Bobroff |
| 2014/0128239 | A1* | 5/2014 | Murphy ............... A61M 1/3696 494/2 |
| 2015/0273132 | A1* | 10/2015 | Ragusa .................. B04B 11/02 494/6 |
| 2017/0246376 | A1 | 8/2017 | Schwarz et al. |

FOREIGN PATENT DOCUMENTS

| | | |
|---|---|---|
| EP | 0573117 A1 | 12/1993 |
| EP | 0682953 A1 | 11/1995 |
| EP | 0771570 A1 | 5/1997 |
| EP | 1166806 | 1/2002 |
| GB | 2250699 A | 6/1992 |
| JP | H04-236960 A | 8/1992 |
| JP | H11-506030 A | 6/1999 |
| JP | 2008-538514 A | 10/2008 |
| WO | 1984/00892 A1 | 3/1984 |
| WO | 1989/01792 A1 | 3/1989 |
| WO | 1989/04709 A1 | 6/1989 |
| WO | 1994/21311 A2 | 9/1994 |
| WO | 1995/03840 A1 | 2/1995 |
| WO | 1996/40319 A1 | 12/1996 |
| WO | 1998/14163 A1 | 4/1998 |
| WO | 2000/38756 A1 | 7/2000 |
| WO | 2006/100651 A1 | 9/2006 |

OTHER PUBLICATIONS

International Search Report and Written Opinion for Application No. PCT/US2017/038761, dated Oct. 30, 2017, 12 pages.

* cited by examiner

SYSTEM AND METHOD FOR CONTINUOUS FLOW RED BLOOD CELL WASHING

CROSS-REFERENCE TO RELATED APPLICATIONS

This patent application is a 35 U.S.C. § 371 national stage filing of International Application No. PCT/US2017/038761, filed on Jun. 22, 2017, which claims priority from U.S. Provisional Patent Application No. 62/354,162, filed on Jun. 24, 2016, entitled "System and Method for Continuous Flow Red Blood Cell Washing," assigned attorney docket number 1611/C73, and naming Dominique Uhlmann as inventor. The disclosure of each of the foregoing applications is incorporated herein, in its entirety by reference.

TECHNICAL FIELD

The present invention relates to washing blood components, and more particularly to washing packed red blood cells using a continuous flow separation device.

BACKGROUND ART

Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma.

After the procedure is complete, the collected blood components may be further processed and/or stored for later use. In some instances, the collected blood components (e.g., red blood cells) may be mixed with a storage solution prior to storage. Although this storage solution may help prolong the life of the stored blood component, in some instances and for some therapeutic treatments, it may need to be removed prior to infusion/transfusion. Additionally, in some instances, the blood component may deteriorate to some degree during storage. To remove the storage solution and any deteriorated component (e.g., lysed cells), it may be beneficial to wash the blood component prior to infusion/transfusion.

SUMMARY OF THE EMBODIMENTS

In accordance with one embodiment of the present invention, a method for continuously washing packed red blood cells includes (1) connecting a wash solution container to a wash solution line and (2) connecting a red blood cell container to a red blood cell line. The wash solution line may fluidly connect the wash solution container and an inlet line of a blood component separation device. The red blood cell line may fluidly connect the red blood cell container and the inlet line of the blood component separation device. The red blood cell container may contain a volume of packed red blood cells. The method may then transfer, at a first flow rate, packed red blood cells from the red blood cell container to the blood component separation device, and transfer, at the same time as the packed red blood cells, wash solution from the wash solution container to the blood component separation device. The wash solution may be transferred at a second flow rate that is greater than the first flow rate. The wash solution may mix with the packed red blood cells in the inlet line to dilute and wash the packed red blood cells (e.g., prior to entering the separation device). The blood component separation device may separate the washed red blood cells from the wash solution and a supernatant.

The method may also monitor the volume of washed red blood cells collected within the blood component separation device, and begin drawing the washed red blood cells from the blood component separation device (e.g., into a red blood cell product container) when a target volume of red blood cells is collected within the blood component separation device. Additionally or alternatively, the method may monitor the volume of packed red blood cells remaining within the red blood cell container, and stop the transfer of packed red blood cells when the red blood cell container is empty. The method may also reduce the transfer of wash solution from the second flow rate to a third flow rate.

In some embodiments, transferring the packed red blood cells to the blood component separation device may include pumping, with a red blood cell pump, the packed red blood cells into the blood component separation device. Similarly, transferring wash solution to the blood component separation device may include pumping, with a wash solution pump, the wash solution into the blood component separation device. In such embodiments, the method may stop the red blood cell pump when the red blood cell container is empty and/or stop the wash solution pump when all washed red blood cells have been drawn from the blood component separation device.

In additional embodiments, the method may monitor the volume of washed red blood cells within the blood component separation device, and stop drawing washed red blood cells from the blood component separation device when no washed red blood cells remain within the blood component separation device. The method may then isolate the red blood cell product container, stop the wash solution pump to stop transferring wash solution to the blood component separation device, and/or stop the centrifuge. The ratio of the first flow rate to the second flow rate may be between 1:2 and 1:5 (e.g., 1:3). The first flow rate may be between 10 and 30 milliliters per minute (e.g., 20 milliliters per minute), the second flow rate may be between 20 and 150 milliliters per minute (e.g., 60 milliliters per minute), and the third flow rate may be between 10 and 40 milliliters per minute (e.g., 20 milliliters per minute). The target volume of washed red blood cells may be between 50 and 150 milliliters (e.g., 100 milliliters). The blood component separation device may be a centrifuge bowl and the wash solution may be saline.

In accordance with further embodiments of the present invention, a system for continuous washing of packed red blood cells includes a blood component separation device, an inlet line, a red blood cell line, a wash solution line, a washed red blood cell line, and a waste line. The separation device may separate packed red blood cells from a wash solution and a supernatant, and may have an inlet, a red blood cell outlet, and a waste outlet. The inlet line may be fluidly connected to the inlet of the blood component separation device, and may allow dilution of the packed red blood cells with wash solution prior to entering the blood component separation device. The red blood cell line may be fluidly connected to the inlet line and may be connected to a packed red blood cell container. The flow through the red blood cell line may be controlled by a red blood cell pump. The wash solution line may be fluidly connected to the inlet line and a wash solution container, and the flow through the wash solution line may be controlled by a wash solution pump. The washed red blood cell line may be fluidly connected to the red blood cell outlet of the blood component separation device and a red blood cell product container. The flow through the washed red blood cell line may be controlled by a washed red blood cell pump. The waste line may be fluidly connected to the waste outlet of the blood component separation device and a waste container.

The system may also have a controller that controls the operation of the red blood cell pump, the wash solution pump and the washed red blood cell pump to control fluid flow through the system. Additionally, the system may have a pressure sensor that is located on the washed red blood cell line and measures the pressure within the washed red blood cell line. A line sensor located on the waste line may monitor the fluid passing through the waste line.

In some embodiments, the blood component separation device may be a centrifuge bowl. In such embodiments, the bowl may include an outer body, a top core, and a separation region. The outer body may be rotatable about a longitudinal axis of the centrifuge bowl and may have (1) a main body defining an interior cavity, (2) a neck portion extending proximal to the main body, and (3) a shoulder connecting the main body and the neck portion. The top core may be located within and rotatable with the outer body, may be coaxial with the outer body, and may include a chimney extending through it along the longitudinal axis of the centrifuge bowl. The separation region may be located between the top core and the outer body, and rotation of the centrifuge bowl may separate the packed red blood cells from the wash solution and supernatant.

The bowl may also include an inlet port, a first outlet port and a second outlet port. The inlet port may be used to introduce the packed red blood cells and wash solution into the centrifuge bowl. An inlet tube may fluidly connect to and extend distally from the inlet port and through the chimney. The inlet tube may introduce the packed red blood cells and wash solution into an introduction region. The first outlet port may be used to draw washed red blood cells out of the centrifuge bowl, and an extraction tube may extend from the first outlet port to an extraction region. The second outlet port may be fluidly connected to the separation region, and may allow wash solution and supernatant to exit the centrifuge bowl.

In some embodiments, the bowl may include a bottom core located within and rotatable with the outer body. The bottom core may be located between the bottom of the outer body and the top core, and the extraction region may be located between the bottom wall of the bottom core and the bottom of the outer body. The extraction region may fluidly connect the extraction tube and the separation region. The extraction tube may extend through the bottom core. The bowl may also have a seal member located between the extraction tube and the bottom core that prevents leakage between them.

In other embodiments, the bottom core may have a proximally extending wall that extends from the bottom wall. The proximally extending wall may be radially outward from at least a portion of the top core. The centrifuge bowl may have a primary separation region defined by the proximally extending wall and at least a portion of the top core. The primary separation region may be fluidly connected to the separation region. The centrifuge bowl may further include a fluid pathway fluidly connecting the inlet tube and the primary separation region. The fluid pathway may extend between a bottom wall of the top core and the bottom wall of the bottom core. The extraction region may be located between the bottom wall of the bottom core and a bottom of the outer body, and the extraction tube may extend into the extraction region. The proximally extending wall may prevent separated wash solution and supernatant from entering the extraction region. The washed red blood cell pump may draw the washed red blood cells from the centrifuge bowl.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Figure 1:
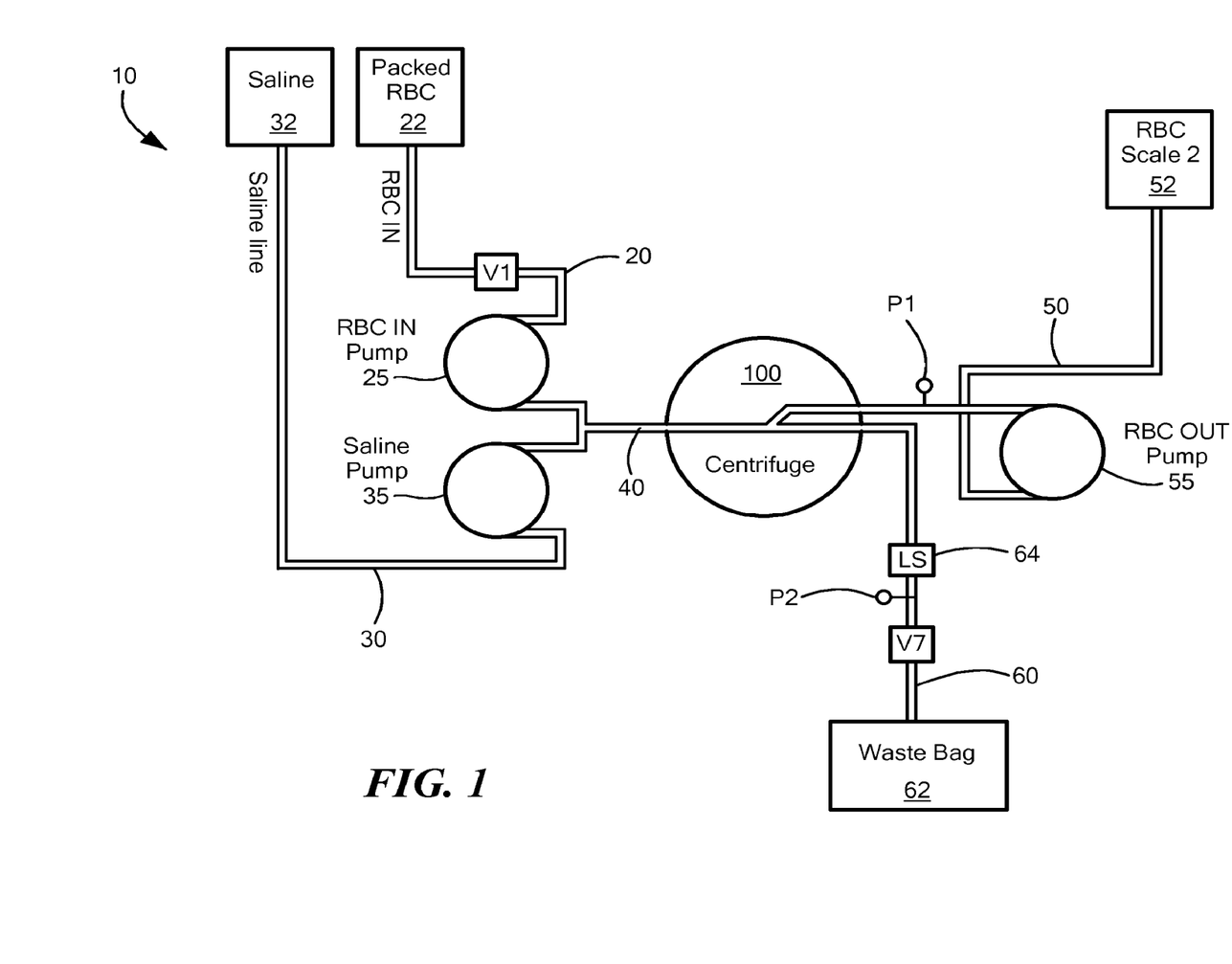
FIG. 1 schematically shows a system for washing packed red blood cells using a continuous flow separation device, in accordance with some embodiments of the present invention.

FIG. 1 schematically shows a system 10 for washing packed red blood cells in accordance with various embodiments of the present invention. The system 10 includes a blood processing device having a blood component separation device 100 (e.g., a continuous flow separation device such as that described within U.S. application Ser. No. 14/072,220, incorporated herein by reference) with a processing chamber in which packed red blood cells may be separated from wash solution and supernatant (discussed in greater detail below). To facilitate the introduction of red blood cells into the separation device 100, the system 10 includes a red blood cell line 20 that is connected to a red blood cell container 22 (e.g., a unit of packed red blood cells) containing a volume of packed red blood cells. Similarly, to facilitate the introduction of wash solution (e.g., saline) into the separation device 100, the system 10 may include a wash solution line 30 that is connected to a wash solution container 32 containing a volume of wash solution/saline. Both the red blood cell line 22 and the wash solution line 32 are fluidly connected to the inlet 190 (FIG. 2) of the separation device 100, for example, via an inlet line 40.

To collect a red blood cell product from the separation device 100 after processing/washing the packed red blood cells, the system 10 includes a washed red blood cell line 50 that fluidly connects to a red blood cell outlet 220 of the separation device 100 and a red blood cell product container 52 in which the processed/washed red blood cells may be collected. Additionally, the system 10 may include a waste line 60 that fluidly connects to a waste outlet 230 on the separation device 100 and to a waste container 62 in which any waste product (e.g., removed wash solution and/or supernatant) may be collected.

As discussed in greater detail below, the flow through the red blood cell line 20, the saline line 30, and the washed red blood cell line 50 may be controlled via a pump on each of the lines 20/30/50. For example, the system 10 may include (1) a red blood cell pump 25 located on the red blood cell line 20 that draws the packed red blood cells from the red blood cell container 22, (2) a wash solution pump 35 located on the wash solution line 30 that draws wash solution (e.g., saline) from the wash solution container 32, and (3) a washed red blood cell pump 55 on the washed red blood cell line 50 that draws the washed red blood cells from the separation device 100. The system controller may control the speed of each of the pumps 25/35/55 to control the flow rate through each of the lines 20/30/50.

At various points, the system 10 may include valves that allow the user and/or the system 10 (e.g., the controller within the system 10) to appropriately direct fluid through the system 10. For example, the system 10 may include a valve V1 located on the red blood cell line 20 to selectively prevent and allow packed red blood cells to flow through the red blood cell line 20. Similarly, the system 10 may include a valve V7 on the waste line 60 to selectively prevent and allow fluid flow through the waste line 60 (e.g., an into the waste container 62). Additionally, although not shown, the system 10 may include a valve on the saline line 30 to stop the flow of saline from the saline container 32 as needed.

To monitor the fluid exiting the blood component separation device 100 and flowing into through the waste line 60, the system 10 may include a line sensor 64 located on the waste line 60. For example, the line sensor 64 may be an optical sensor that consists of an LED which emits light through fluid (e.g., saline and/or blood components) passing through the waste line 60 and a photo detector which receives the light after it passes through the fluid. The amount of light received by the photo detector is correlated to the density of the fluid passing through the line. For example, when wash solution is leaving the separation device 100, the amount of light received by the photo detector will be greater than if red blood cells are passing through the waste line 60 (e.g., the level of transmission is greater for the wash solution as compared to red blood cells). The line sensor 64 may be in communication with the system controller to allow the controller to adjust the speed of the pumps 25/35/55. For example, if the line sensor 64 detects red blood cells within the waste line 60, the controller may lower the speed of the packed red blood cell pump 25.

It should be noted that, in many applications, it is important to monitor the pressures within the system 10 and lines 20/30/40/50/60 to ensure that the system 10 is operating properly and the pressure within the system 10 is not too high or too low. To that end, the system 10 may include pressure sensors on one or more of the lines 20/30/40/50/60 to measure the pressures at various points in the system 10. For example, the system 10 may include a pressure sensor P1 on the washed red blood cell line 50 and/or a pressure sensor P2 on the waste line 60. These pressure sensors P1/P2 monitor the pressures within their respective lines 50/60 to ensure that the pressures do not go above or below a threshold (e.g., which can indicate a problem with the procedure and/or system 10, such as a problem with the integrity of the seal on the separation device 100). The pressure sensors P1/P2 may be in communication with the controller such that, if the pressure drops below or goes above a threshold, the controller may adjust the flow rates through the lines 20/30/40/50/60 (e.g., by adjusting the pumps 25/35/55), and/or stop the procedure.

Figure 2:
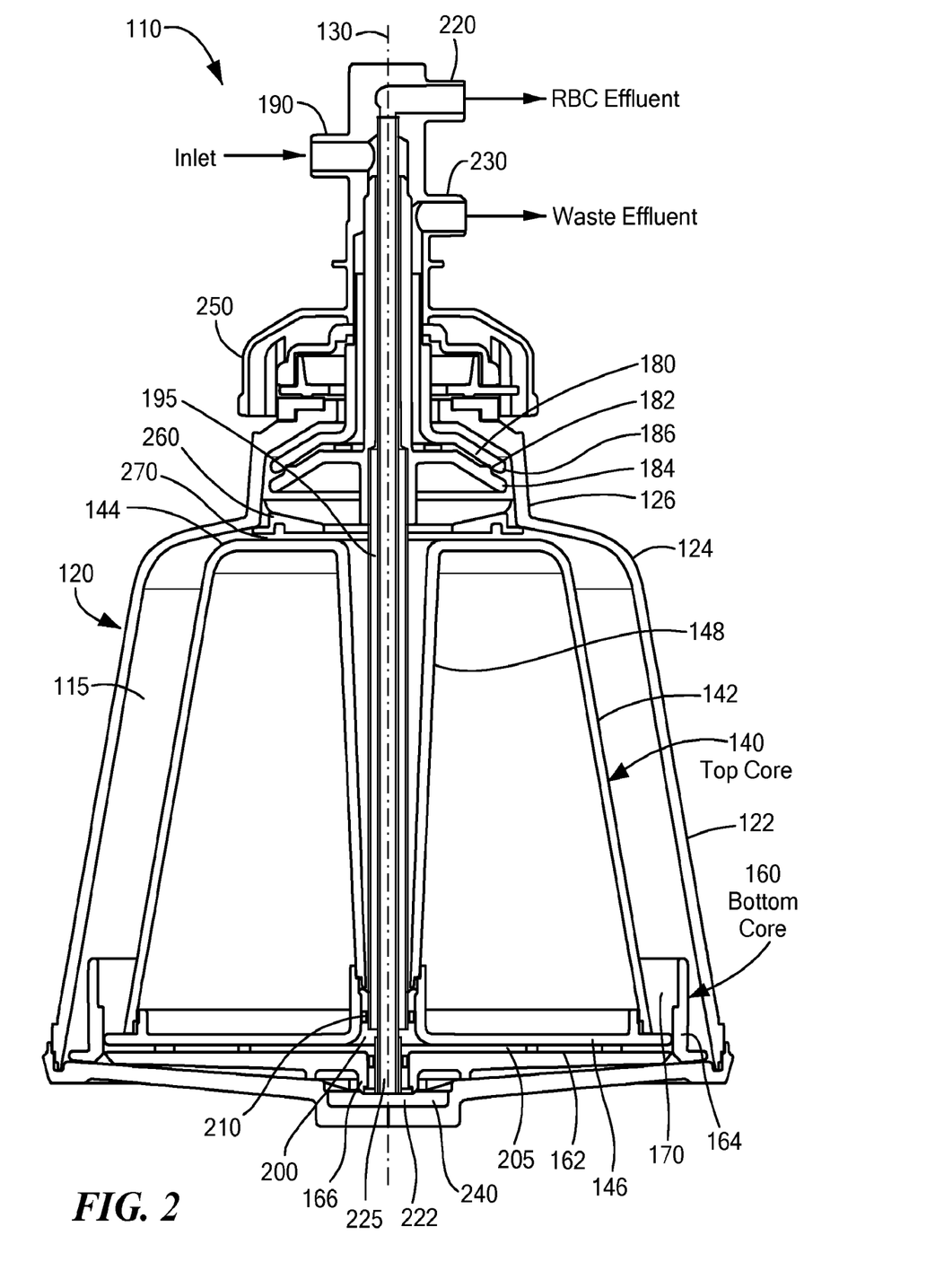
FIG. 2 schematically shows a cross-sectional view of a continuous flow centrifuge bowl for use within the system shown in FIG. 1, in accordance with illustrative embodiments of the present invention.

FIG. 2 schematically shows a cross-section of a continuous flow separation device 100 (e.g., a centrifuge bowl 110), in accordance with some embodiments of the present invention. The bowl 110 has an outer body 120 that defines the structure of the bowl 110 and an inner volume into which the packed red blood cells and wash solution may be introduced for processing. The outer body 120, in turn, includes a main wall 122, a neck portion 126, and shoulder portion 124 that connects the main wall 122 and the neck portion 126. As discussed in greater detail below, the bowl 110 is rotatable about an axis 130 in order to separate the packed red blood cells from the wash solution and/or supernatant.

Within the interior of the outer body 120, the bowl 110 can include a number of cores that displace some of the volume within the outer body 120, create separation regions in which the red blood cells separate from the wash solution and supernatant, and create a number of fluid paths/channels within the bowl 110. For example, the bowl 110 may include a top core 140 that fills a significant portion of the inner volume and may be frusto-conical in shape. The top core 140 includes a top surface 144, a bottom wall 146, and a side wall 142 that extends between the top surface 144 and the bottom wall 146. The side wall 142 may be spaced from the main wall 122 to create a separation region (e.g., a secondary separation region 115) between the side wall 142 of the top core 140 and the main wall 122 of the outer body 120. Additionally, the top core 140 can have a chimney 148 extending through the center from the top surface 144 to the bottom wall 146. The chimney 148 may serve as a channel through which a number of tubes (e.g., an inlet tube and an extraction tube) can pass.

Figure 3:
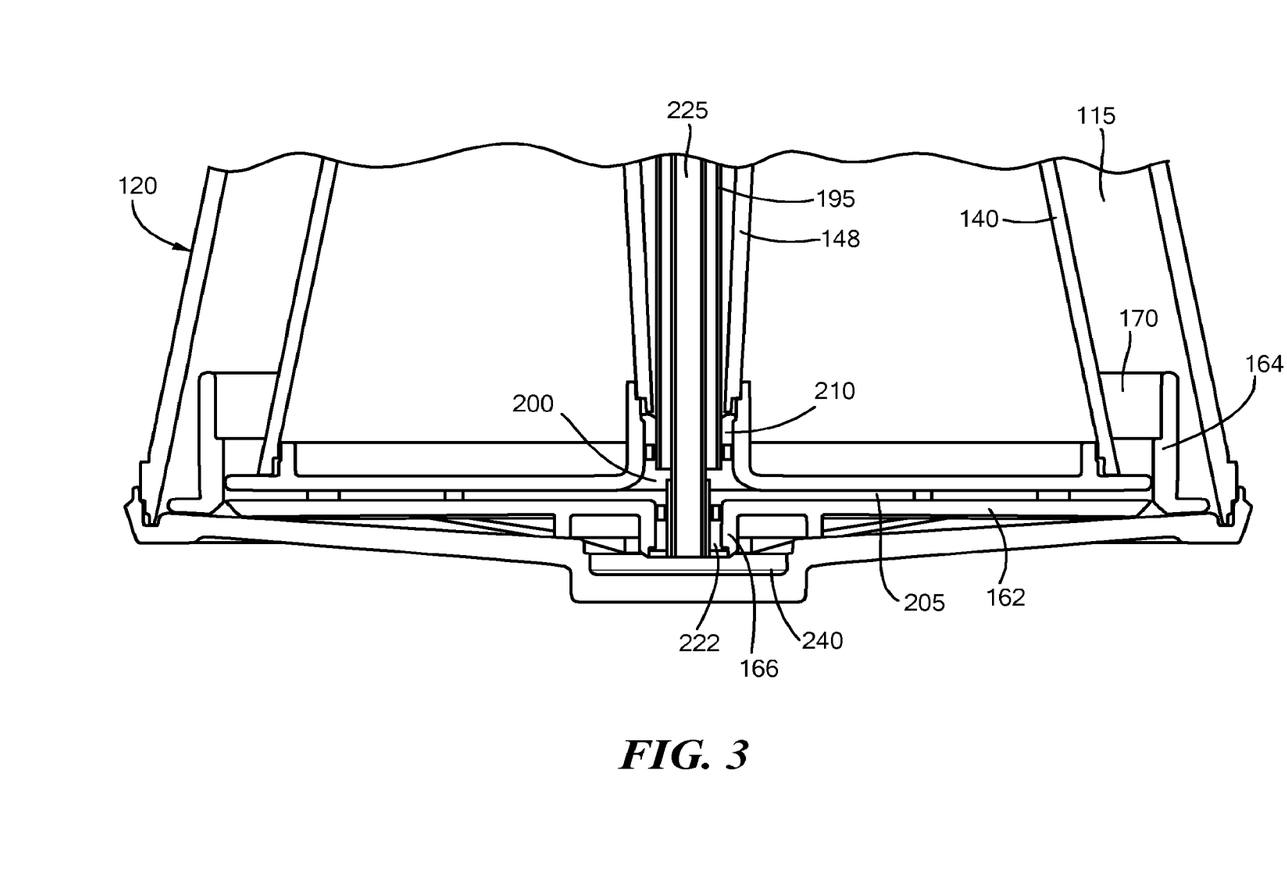
FIG. 3 schematically shows a cross-sectional view of the lower portion of the centrifuge bowl shown in FIG. 2 with an alternative bottom core, in accordance with illustrative embodiments of the present invention.

The bowl 110 may also include a bottom core 160 (FIG. 3) located below the top core 130 (e.g., distal to the top core 130). The bottom core 160 may include a bottom circular wall 162 with an opening 166 extending through it (e.g., near the center of the circular wall 162). The bottom core 160 may also have a vertical wall 164 that extends upward (e.g., proximally) from the bottom circular wall 162. As shown in FIGS. 2 and 3, the vertical wall 164 is located near the outer diameter of the bottom circular wall 162 and may extend upwards such that it is radially outward from the side wall 142 of the top core 140. The annular space between the side wall 142 of the top core 140 and the vertical wall 164 creates a primary separation region 170 in which the red blood cells begin to separate from the wash solution/supernatant (discussed in greater detail below). Although similar, it is important to note that the bottom core 160 shown in FIG. 3 is an alternative embodiment of the bottom core 160 shown in FIG. 2 (e.g., it is thinner than that shown in FIG. 2).

Figure 5:
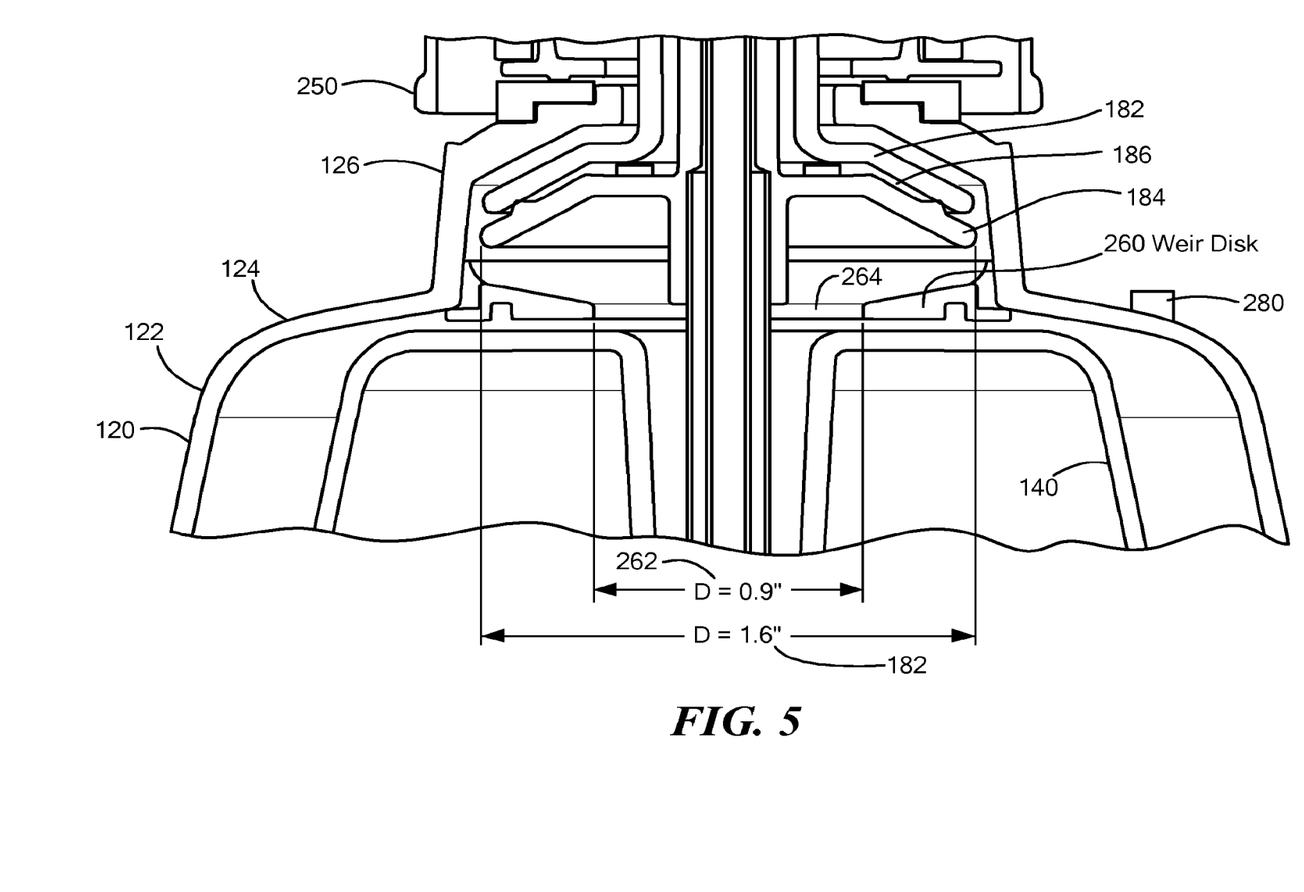
FIG. 5 schematically shows a cross-sectional view of the top portion of the centrifuge bowl shown in FIG. 2, in accordance with illustrative embodiments of the present invention.

As best shown within FIG. 5, within the neck portion 126 of the outer body 120, the centrifuge bowl 110 can include a upper skirt 182 and a lower skirt 184 both extending radially outward from the center of the bowl 110. Together, the upper skirt 182 and the lower skirt 184 can form an effluent skirt 180 through which waste (e.g., separated wash solution and supernatant) can flow and exit the bowl 110 (e.g., via the waste outlet 230). To that end, the upper skirt 182 and the lower skirt 184 may be spaced from one another such that an effluent channel 186 is formed between the skirts 182/184. The exiting waste can flow through the effluent channel 186 to reach the waste outlet 230.

In order to facilitate the transfer of fluids (e.g., packed red blood cells, wash solution, washed red blood cells, and waste) in and out of the centrifuge bowl 110, the bowl 110 can have an inlet and one or more outlets. For example, the bowl 110 may include an inlet 190 that may be used to introduce the packed red blood cells and wash solution into the bowl 110. In many blood processing procedures, it is desirable to introduce the incoming blood components (e.g., the packed red blood cells) into an area near the bottom of the bowl 110. To that end, some embodiments of the bowl 110 may also include an inlet tube 195 that extends downward from the inlet 190, through the chimney 148 in the top core 140, and into an introduction region 200 located between the top core 140 and the bottom core 160. Additionally, the bottom core 160 (e.g., the circular wall 162) may be spaced from the bottom 146 of the top core 140 to create a channel 205 extending from the introduction region 200 to the primary separation region 170. The centrifugal force created by spinning the bowl 110 may cause the packed red blood cells and wash solution entering the introduction region 200 to flow through the channel 205 and into the primary separation region 170.

Figure 4:
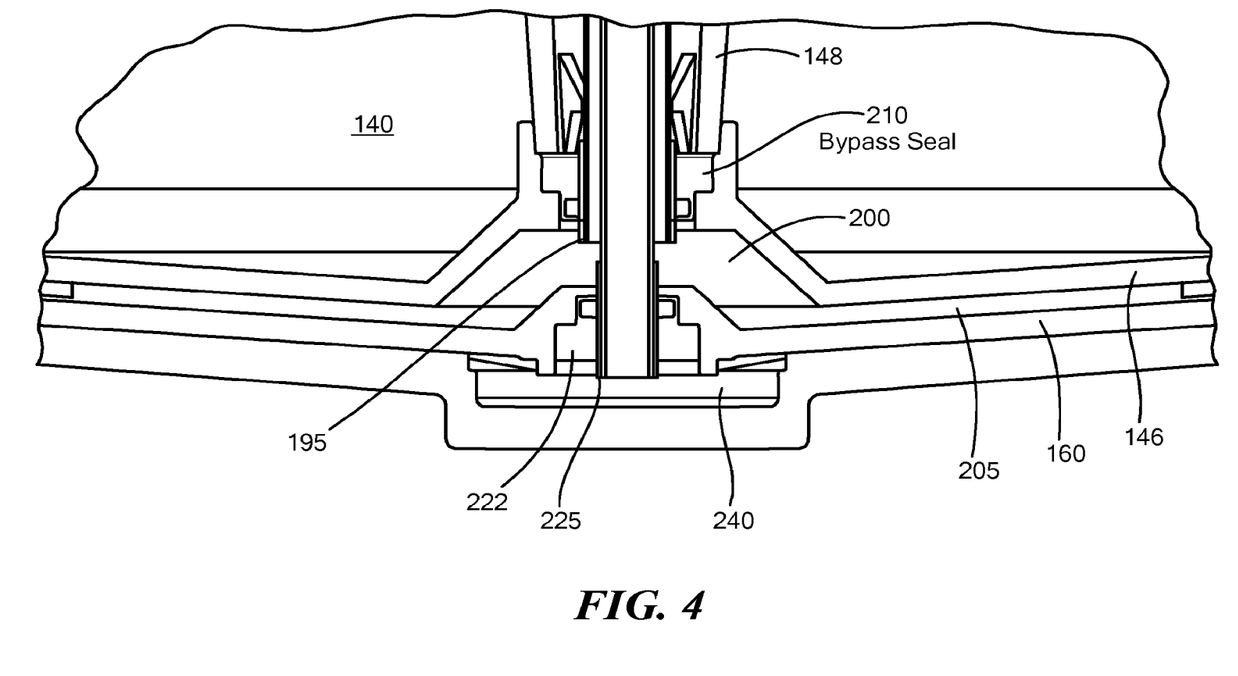
FIG. 4 schematically shows a cross-sectional view of a bypass seal within the centrifuge bowl shown in FIG. 2, in accordance with illustrative embodiments of the present invention.

It is important to note that problems can arise if the fluid introduced into the bowl 110 (e.g., into the introduction region 200) flows back up into the chimney 148 (e.g., instead of traveling towards the outer diameter of the bowl 110 and into the separation regions). For example, if this "bypass" occurs while the bowl 110 is being filled, some of the fluid (e.g., packed red blood cells, wash solution, etc.) may flow up the chimney 148, and into the region around the effluent skirt 180. This, in turn, may reduce the collection efficiency of the system and/or negatively impact the quality of the final product (e.g., the hematocrit of the washed red blood cells). In order to avoid this "bypass" and isolate the introduction region 200 from the chimney 148 in the top core 130, the bowl 110 may include a bypass seal 210 (FIG. 4) located between the outer diameter of the inlet tube 195 and the inner diameter of the chimney 148. The bypass seal 210 can be a rotary seal to allow the top core 130 (and the bowl 110) to rotate relative to the inlet tube 195 (which does not rotate during bowl operation).

In addition to the inlet 190, the bowl 110 can also include a washed red blood cell outlet 220 and a waste outlet 230. As the name suggests, the washed red blood cell outlet 220 can be used to remove washed red blood cells from the bowl 110. Additionally, in a manner similar to the inlet 190, the washed red blood cell outlet 220 may be fluidly connected to a tube (e.g., an extraction tube 225) that extends downward from the washed red blood cell outlet 220, through the chimney 148, through the opening 166 in the bottom core 160 (e.g., within the bottom circular wall 162), and into a washed red blood cell extraction region 240 located below the bottom bore 160 (e.g., between the bottom core 160 and the bottom of the bowl 110). To prevent leakage past the bottom core 160 (e.g., through opening 166), the bowl 110 can also have a seal 222 (e.g., a rotary seal) between the extraction tube 225 and the opening 166. As discussed in greater detail below, the washed red blood cell pump 55 can draw the washed red blood cells out of the extraction region 240, through the extraction tube 225 and out of the washed red blood cell outlet 220.

The waste outlet 230 may be used to remove the waste (e.g., the separated wash solution and supernatant) from the bowl 110. To that end, the waste outlet 230 may be fluidly connected to the effluent channel 186 through the effluent skirt 180. Therefore, when the waste is pushed towards the neck portion 126 (e.g., as discussed in greater detail below), the waste can flow through the effluent channel 186 and out of the waste outlet 230.

As best shown in FIGS. 2 and 5, the centrifuge bowl 110 may include a rotary seal 250 that connects the ports (e.g., the inlet 190, washed red blood cell outlet port 220, and waste outlet port 230) to the outer body 120 of the bowl 110. The rotary seal 250 allows the bowl 110 (and the top core 140 and bottom core 160) to spin while the inlet 190, washed red blood cell outlet 220, and waste outlet 230 remain stationary.

In order to reduce the pressure required to withdraw the washed red blood cells, some embodiments of the bowl 110 can include a weir disk 260 (FIG. 5) that extends radially inward from the bottom of the neck portion 126 of the outer body 120. The weir disk 260 essentially creates a wall that forces any waste leaving the bowl 110 to a smaller diameter defined by the inner diameter 262 of the opening 264 through the weir disk 260. By reducing this diameter, the weir disk 260 reduces the pressure required to withdraw the washed red blood cells from the bowl 110.

As shown in FIG. 5, the weir disk 260 creates a fluid channel 270 between the weir disk 260 and the top surface 144 of the top core 140. As the bowl 110 fills with fluid, the fluid (e.g., the waste) will flow through the fluid channel 270 between the weir disk 260 and the top surface 144 of the top core 140 until it reaches the opening 264 in the weir disk 260. The fluid may then "roll over" the weir disk 260 (e.g., similar to the overflow of a dam), and fill the region above the weir disk 260 (e.g., the neck portion 126 of the bowl 110) until it comes in contact with the effluent skirt 180. The fluid (e.g., the separated wash solution and/or supernatant) may then be pushed from the bowl 110 into the effluent channel 186 and into the waste outlet 230.

During processing (e.g., washing of the packed red blood cells) it may be important to know not only how full the bowl 110 is but also the location of the washed red blood cells and/or the volume of the washed red blood cells within the bowl 110. To that end, some embodiments may include an optical system 280 located on the bowl 110. The optical system 280 may include an LED (e.g., a red LED) that emits a beam (e.g., approximately 1-2 mm in diameter) that illuminates a small area of the shoulder 124 (or other portion of the bowl 110). Additionally, the optical system 280 may also include an optical sensor that is focused on the illuminated area of the bowl shoulder 280 (or other portion of the bowl 110) and determines the location of the red blood cells within the bowl 110 (e.g., based on a signal level received back at the sensor).

Figure 6:
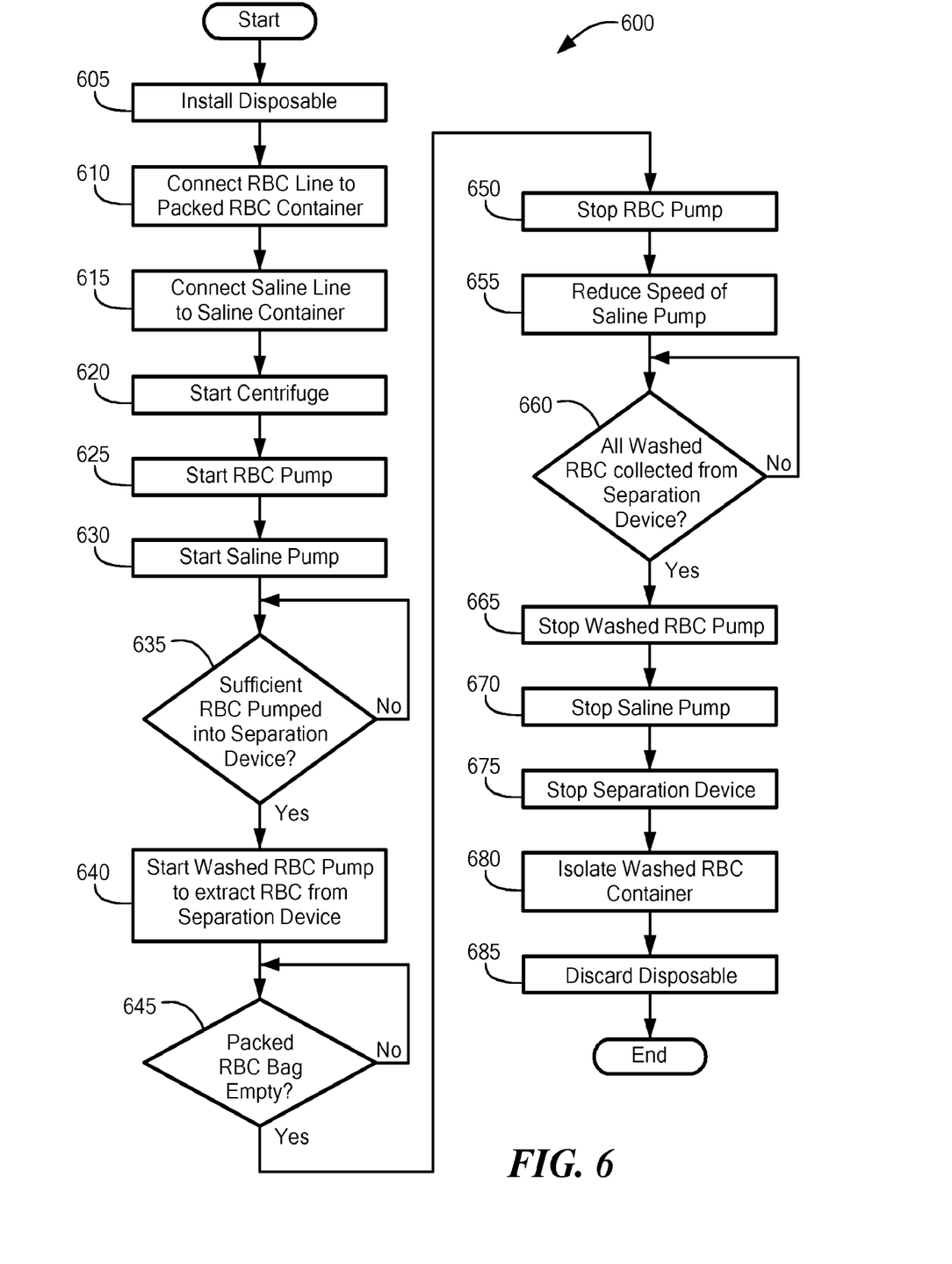
FIG. 6 is a flowchart depicting a method of washing packed red blood cells using the system shown in FIG. 1, in accordance with various embodiments of the present invention.
Figure 7A:
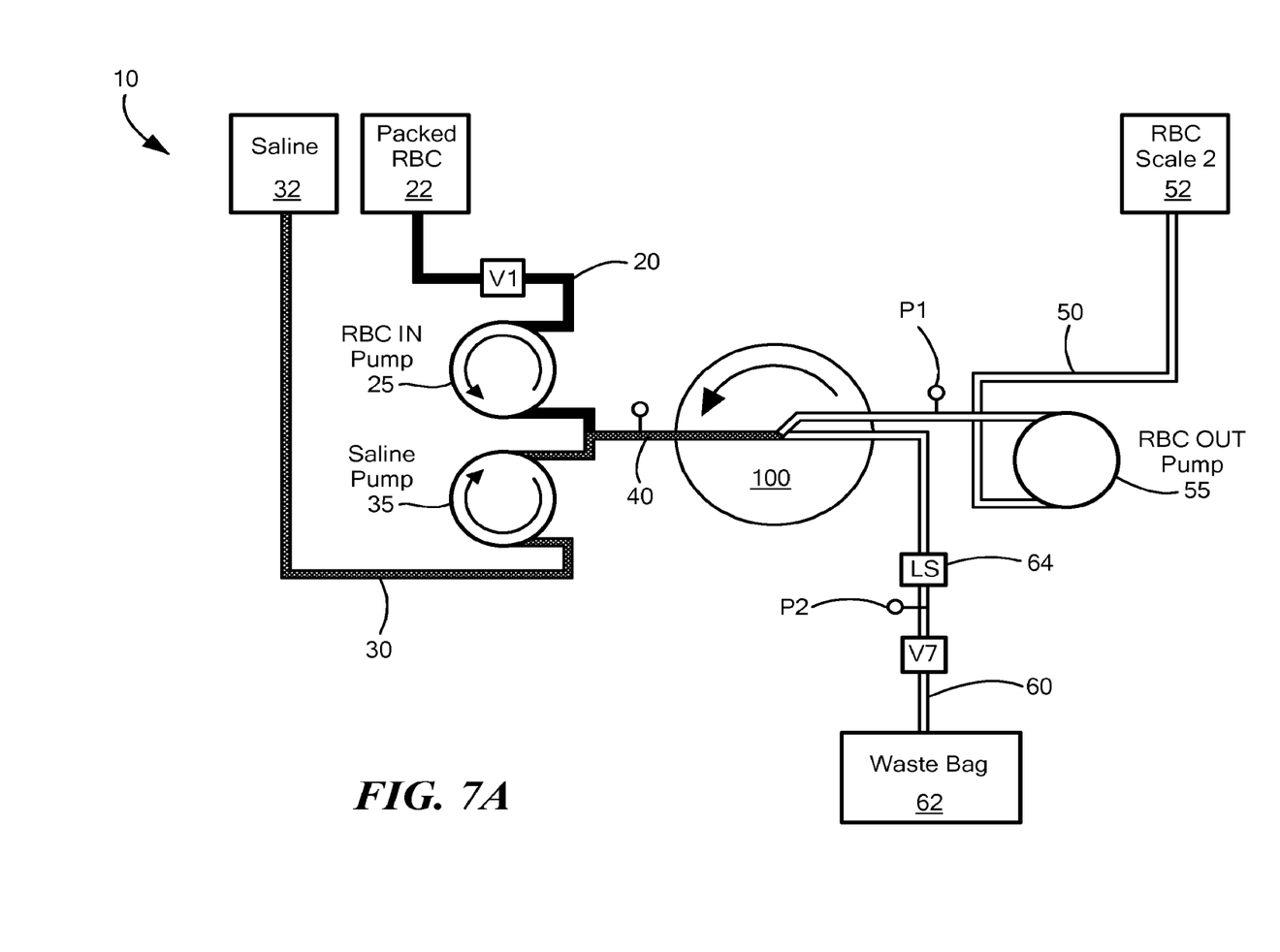
FIGS. 7A and 7B schematically show the system shown in FIG. 1 at various stages of the method shown in FIG. 6, in accordance with some embodiments of the present invention.
Figure 7B:
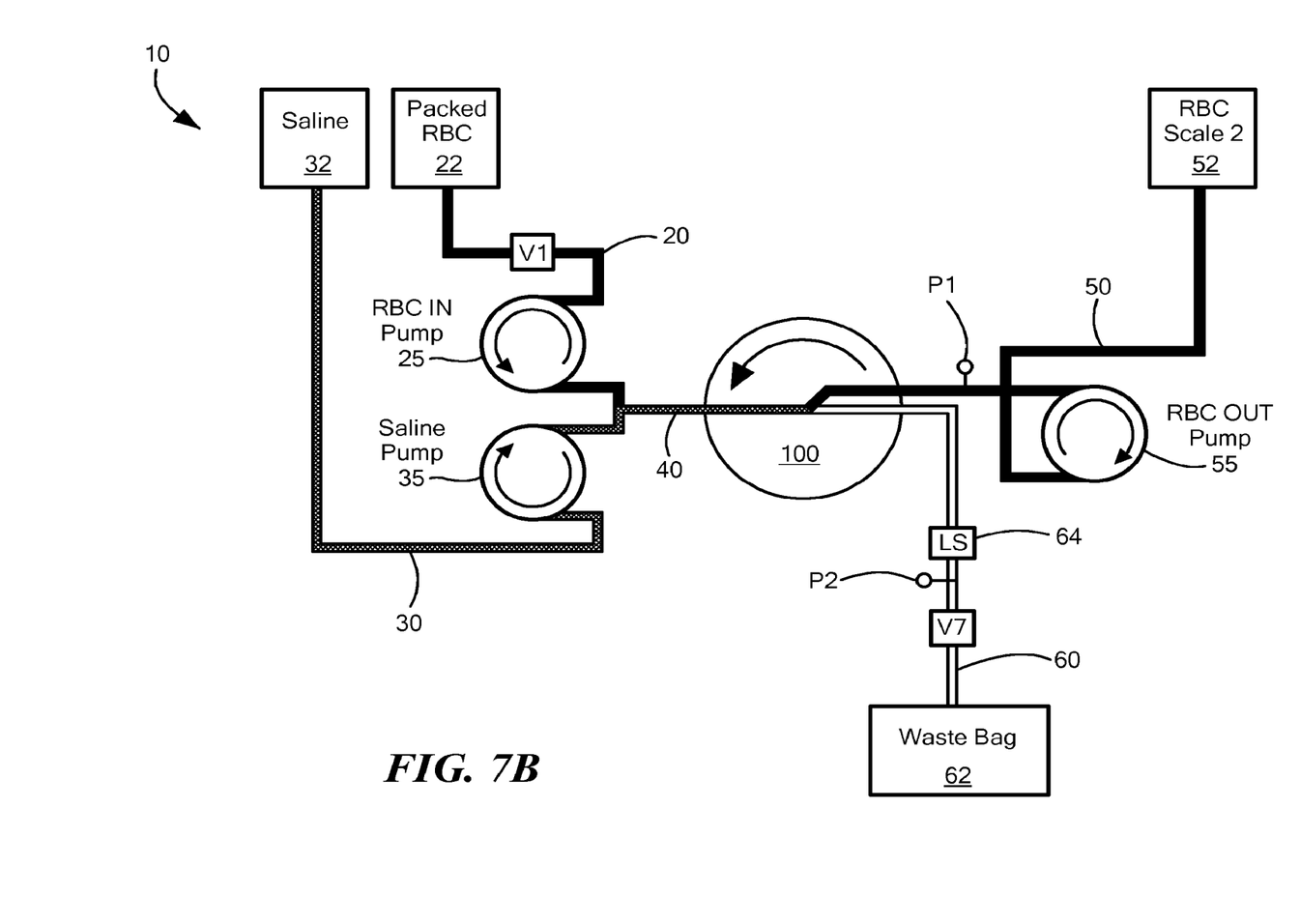

FIG. 6 is a flowchart depicting a method 600 of washing packed red blood cells in accordance with various embodiments of the present invention. FIGS. 7A and 7B schematically show the system 10 at various stages of the method.

First, the user may install the disposable set shown in FIG. 1 into the system 100 (Step 605), for example, by installing the separation device 100 and running the lines 20/30/40/50/60 through their respective valves V1/V7 and pumps 25/35/55. Once the disposable set is installed, the user may then connect the red blood cell line 20 to the packed red blood cell container 22 (Step 610) and connect the wash solution line 30 to the wash solution container 32 (step 615).

After the disposable set is installed and the red blood cell line 20 and wash solution line 30 are connected, the system 10/method 600 may then start rotating the centrifuge 110. The speed at which the system 10/method 600 rotates the separation device 100 (e.g., bowl 110) may depend on a number of factors including, for example, the volume of packed red blood cells to be washed, the hematocrit of the packed red blood cells, etc. However, in some embodiments, the system 10/method 600 may rotate the separation device 100 at speeds between 3500 and 5000 revolutions per minute (e.g., 4000 RPM). Once the bowl 110 is up to speed, the system 10 (e.g., the controller) may activate the red blood cell pump 25 (Step 625) to start drawing packed red blood cells from the red blood cell container 32 and activate the wash solution pump 35 (Step 630) to start drawing wash solution from the wash solution container 32 (FIG. 7A).

As mentioned above, both the red blood cell line 20 and the wash solution line 30 are connected to the inlet line 40 (which, in turn, is connected to the inlet 190 of the bowl 110). To that end, as the packed red blood cells and the wash solution reach the inlet line 40 (and prior to entering the bowl 110), they will mix together and the wash solution will dilute the packed red blood cells prior to entering the bowl 110. This dilution and mixing as the packed red blood cells enter the inlet line 40 allows the wash solution to essentially get between the packed red blood cells and begin to wash out the supernatant and/or any storage solution contained within the packed red blood cells.

It is important to note that the flow rates at which the packed red blood cells and wash solution are drawn from their respective containers 22/32 (and the ratio between the flow rates) and introduced into the bowl 110 impact the level of washing of the packed red blood cells (e.g., how much supernatant is washed out of the red blood cells). To that end, some embodiments utilize a packed red blood cell to wash solution flow rate ratio of between 1:2 and 1:5 (e.g., 1:3). For example, the flow rate for the packed red blood cells may be between 10 and 30 ml/min (e.g., 20 ml/min) and the flow rate for the wash solution may be between 20 and 150 ml/min (e.g., 60 ml/min).

As the packed red blood cell/wash solution mixture (e.g., the diluted packed red blood cells) enters the bowl 110 through the inlet 190, it will flow down the inlet tube 195 and into the introduction region 200. Once in the introduction region 200, the centrifugal forces from the spinning of the bowl 110 will cause the packed red blood cell/wash solution mixture to flow through the channel 205 between the top core 140 and bottom core 160 and into the primary separation region 170 (e.g., between the side wall 142 of the top core 140 and the proximally extending wall 164 of the bottom core), where separation of the packed red blood cells from the wash solution and supernatant begins.

As additional packed red blood cell/wash solution mixture is introduced into the bowl 110, the packed red blood cell/wash solution mixture will flow into the secondary separation region 115 where the packed red blood cell/wash solution mixture continues to separate. For example, as the packed red blood cell/wash solution mixture enters the secondary separation region 115 of the bowl 110, the centrifugal forces cause the heavier cellular components (e.g., the red blood cells) of the mixture to sediment from the lighter wash solution and supernatant. As the bowl 110 continues to fill with the packed red blood cell/wash solution mixture, the red blood cells will continue to sediment to the outermost diameter, flow over the proximally extending wall 164 on the bottom core 160, and begin to fill the area between the bottom core 160 and the bottom of the bowl 110. As additional washed red blood cells collect, they will begin to pack, increasing the hematocrit of the final product. Additionally, the wash solution and supernatant (e.g., the waste) will move inward towards the center of the bowl 110. When the bowl 110 is full, the separated wash solution/supernatant will flow through the fluid channel 270 between the weir disk 260 and the top surface 144 of the top core 140, over the weir disk 260, and will exit the bowl 110 via the effluent channel 186 and the waste outlet 230. The waste will then flow through the waste line 60 and into the waste container 62.

As mentioned above, the bowl 110 is a continuous flow bowl that allows the continuous washing of the packed red blood cells without the need to intermittently stop. To that end, various embodiments of the present invention also extract washed red blood cells from the bowl 110 as additional packed red blood cell/wash solution mixture is introduced. For example, the system/method may monitor the volume of washed red blood cells collected under the bottom core 160 (e.g., in the extraction region 240) (Step 635), and when a sufficient volume of washed red blood cells has been pumped into the separation device/bowl 110 (e.g., between 80 and 120 mL, for example, 100 mL), the washed red blood cell pump 55 can begin drawing the washed red blood cells up the extraction tube 225 and out of the washed red blood cell outlet 220 (Step 640; FIG. 7B). As the washed red blood cells leave the bowl 110, they will pass through line 50 and into the washed red blood cell container 52.

To ensure that the washed red blood cell pump 55 does not draw the washed red blood cells too quickly and ensure that waste solution is not accidentally drawn out of the bowl 110 through the washed red blood cell outlet 220, the system 10/method 600 may continue to monitor the volume of washed red blood cells collected within the bowl and adjust the speed of the washed red blood cell pump 55 accordingly. For example, the speed of the washed red blood cell pump may range between 10 and 50 mL/min. In some embodiments, the speed of the washed red blood cell pump 55 may be equal to the speed of the red blood cell pump 25 (e.g., 20 ml/min). However, if the system/method detects that the volume of washed red blood cells within the bowl 110 is too low and there is a risk that waste may be drawn up with the washed red blood cells, the controller can reduce the speed of the washed red blood cell pump 55.

During this time, the system 10 (or the user) can monitor (e.g., using a weight sensor, volume sensor, and/or load cell) the volume of packed red blood cells remaining within the packed red blood cell container 22 (Step 645) and, when the packed red blood cell container 22 is empty, the system 10/method 600 may stop the packed red blood cell pump 25 (Step 650). Additionally, to maintain some flow of liquid into the bowl 110, the system 10/method 600 may reduce the speed of the wash solution pump 35 (Step 655). For example, the system 10/method 600 may reduce the speed of the wash solution pump 35 to between 10 and 40 ml/min (e.g., 20 ml) to prevent the bowl 110 (e.g., the rotary seal 250) from overheating.

Once all of the red blood cells have been collected from the bowl 110 (Step 660), the system 10/method 600 may stop the washed red blood cell pump 55 (e.g., to stop drawing washed red blood cells from the bowl 110) (Step 665), stop the wash solution pump 35 (Step 670) to stop the flow of wash solution into the bowl 110, and stop the rotation of the bowl 110 (Step 675). Once the pumps 25/35 and bowl 110 are stopped, the user may isolate (e.g., by heat sealing line 50) the washed red blood cell container 52 from the rest of the system 10 (Step 680) and remove the container 52 for use and/or further processing. The user may then dispose of the rest of the disposable set (e.g., the remaining lines and the bowl 110)(Step 685). It should be noted that, because any wash solution and supernatant remaining in the bowl is waste and will be discarded, there is no need to transfer the wash solution/supernatant to the waste container 62. Rather, the wash solution/supernatant can be disposed of with the bowl 110.

It should be noted that the various embodiments described above are able to efficiently wash-out the supernatant contained within the packed red blood cells and obtain a washed red blood cell product with a high hematocrit level. In particular, systems and method in accordance with the embodiments described above are able to achieve a wash-out of approximately 97% (e.g., 97% of the supernatant is successfully washed out of the packed red blood cells) and a final product hematocrit of greater than 76%. Also, because the systems and methods described are continuous, they are able to wash a wide range of starting packed red blood cell volumes.

It is also important to note that, although the above described system and methods utilize a centrifuge bowl for washing the packed red blood cells, some embodiments of the present invention can be used with different separation devices. For example, the methods described above may be used with "belt" type separation devices such as the Cobe® Spectra system or Cobe® 2991 Cell Processor by Terumo BCT.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method for continuously washing packed red blood cells comprising:
    (a) connecting a wash solution container to a wash solution line, the wash solution line fluidly connecting the wash solution container and an inlet line of a blood component separation device;
    (b) connecting a red blood cell container to a red blood cell line, the red blood cell line fluidly connecting the red blood cell container and the inlet line of the blood component separation device, the red blood cell container containing a volume of packed red blood cells;
    (c) transferring, at a first flow rate, packed red blood cells from the red blood cell container to the blood component separation device;
    (d) transferring, at the same time as step (c), wash solution from the wash solution container to the blood component separation device, the wash solution being transferred at a second flow rate that is greater than the first flow rate, the wash solution mixing with the packed red blood cells in the inlet line, thereby diluting and washing the packed red blood cells, the blood component separation device separating washed red blood cells from the wash solution and a supernatant;
    (e) monitoring a volume of washed red blood cells collected within the blood component separation device;
    (f) drawing washed red blood cells from the blood component separation device and into a red blood cell product container when a target volume of red blood cells is collected within the blood component separation device;
    (g) monitoring a volume of packed red blood cells remaining within the red blood cell container; and
    (h) stopping, when the red blood cell container is empty, the transfer of packed red blood cells and reducing the transfer of wash solution from the second flow rate to a third flow rate.

2. A method according to claim 1, wherein transferring packed red blood cells to the blood component separation device includes pumping, with a red blood cell pump, the packed red blood cells into the blood component separation device.

3. A method according to claim 2, further comprising:
    (i) stopping the red blood cell pump when the red blood cell container is empty.

4. A method according to claim 1, wherein transferring wash solution to the blood component separation device includes pumping, with a wash solution pump, the wash solution into the blood component separation device.

5. A method according to claim 4, further comprising:
    (i) stopping the wash solution pump when all washed red blood cells have been drawn from the blood component separation device.

6. A method according to claim 1, further comprising:
    (i) monitoring the volume of washed red blood cells within the blood component separation device; and
    (j) stopping the drawing of washed red blood cells from the blood component separation device when no washed red blood cells remain within the blood component separation device.

7. A method according to claim 6, further comprising:
    (k) isolating the red blood cell product container after step (j).

8. A method according to claim 6, further comprising:
    (k) stopping the wash solution pump after step (j) to stop transferring wash solution to the blood component separation device.

9. A method according to claim 6, further comprising:
    (k) stopping the centrifuge after step (j).

10. A method according to claim 1, wherein a ratio of the first flow rate to the second flow rate is between 1:2 and 1:5.

11. A method according to claim 10, wherein the ratio of the first flow rate to the second flow rate is 1:3.

12. A method according to claim 1, wherein the first flow rate is between 10 and 30 milliliters per minute.

13. A method according to claim 12, wherein the first flow rate is 20 milliliters per minute.

14. A method according to claim 1, wherein the second flow rate is between 20 and 150 milliliters per minute.

15. A method according to claim 14, wherein the second flow rate is 60 milliliters per minute.

16. A method according to claim 1, wherein the third flow rate is between 10 and 40 milliliters per minute.

17. A method according to claim 16, wherein the third flow rate is 20 milliliters per minute.

18. A method according to claim 1, wherein the target volume of washed red blood cells is between 50 and 150 milliliters.

19. A method according to claim 18, wherein the target volume of washed red blood cells is 100 milliliters.

20. A method according to claim 1, wherein the blood component separation device is a centrifuge bowl.

21. A method according to claim 1, wherein the wash solution is saline.

22. A system for continuous washing of packed red blood cells comprising:
a blood component separation device configured to separate packed red blood cells from a wash solution and a supernatant, the blood component separation device having an inlet, a red blood cell outlet, and a waste outlet;
an inlet line fluidly connected to the inlet of the blood component separation device, the inlet line configured to allow dilution of the packed red blood cells with wash solution prior to entering the blood component separation device;
a red blood cell line fluidly connected to the inlet line and configured to connect to a packed red blood cell container, the flow through the red blood cell line being controlled by a red blood cell pump;
a wash solution line fluidly connected to the inlet line and configured to connect to a wash solution container, the flow through the wash solution line being controlled by a wash solution pump;
a washed red blood cell line fluidly connected to the red blood cell outlet of the blood component separation device and a red blood cell product container, the flow through the washed red blood cell line being controlled by a washed red blood cell pump;
a waste line fluidly connected to the waste outlet of the blood component separation device and a waste container; and
a controller configured to control the operation of the red blood cell pump and the wash solution pump such that wash solution from the wash solution container and packed red blood cells from the packed red blood cell container are transferred to the blood component separation device at the same time and the wash solution mixes with the packed red blood cells in the inlet line, the controller also configured to control the operation of the red blood cell pump at a first flow rate and the operation of the wash solution pump at a second flow rate, the second flow rate being greater than the first flow rate.

23. A system according to claim 22, wherein the controller is further configured to control the operation of the washed red blood cell pump to control fluid flow through the system.

24. A system according to claim 22, further comprising a pressure sensor located on the washed red blood cell line, the pressure sensor configured to measure a pressure within the washed red blood cell line.

25. A system according to claim 22, further comprising a line sensor located on the waste line, the line sensor configured to monitor a fluid passing through the waste line.

26. A system according to claim 22, wherein the blood component separation device is a centrifuge bowl.

27. A system according to claim 26, wherein the centrifuge bowl includes an outer body rotatable about a longitudinal axis of the centrifuge bowl, the outer body having a main body defining an interior cavity, a neck portion extending proximal to the main body, and a shoulder connecting the main body and the neck portion;
a top core located within and rotatable with the outer body, the top core being coaxial with the outer body and including a chimney extending through the top core along the longitudinal axis of the centrifuge bowl;
a separation region located between the top core and the outer body, rotation of the centrifuge bowl separating the packed red blood cells from the wash solution and supernatant;
an inlet port for introducing packed red blood cells and wash solution into the centrifuge bowl;
an inlet tube fluidly connected to and extending distally from the inlet port and through the chimney, the inlet tube configured to introduce the packed red blood cells and wash solution into an introduction region;
a first outlet port for drawing the washed red blood cells out of the centrifuge bowl;
an extraction tube extending from the first outlet port to an extraction region; and
a second outlet port fluidly connected to the separation region, the second outlet port configured to allow wash solution and supernatant to exit the centrifuge bowl.

28. A system according to claim 27, wherein the centrifuge bowl further includes a bottom core located within and rotatable with the outer body, the bottom core located between a bottom of the outer body and the top core, the extraction region located between a bottom wall of the bottom core and the bottom of the outer body, the extraction region fluidly connecting the extraction tube and the separation region.

29. A system according to claim 28, wherein the extraction tube extends through the bottom core.

30. A system according to claim 29, wherein the centrifuge bowl further includes a seal member located between the extraction tube and the bottom core, the seal member preventing leakage between the extraction tube and the bottom core.

31. A system according to claim 28, wherein the bottom core includes a proximally extending wall extending from the bottom wall, the proximally extending wall being radially outward from at least a portion of the top core.

32. A system according to claim 31, wherein the centrifuge bowl further includes a primary separation region defined by the proximally extending wall and at least a portion of the top core.

33. A system according to claim 32, wherein the primary separation region is fluidly connected to the separation region.

34. A system according to claim 32, wherein the centrifuge bowl further includes a fluid pathway fluidly connecting the inlet tube and the primary separation region.

35. A system according to claim 34, wherein the fluid pathway extends between a bottom wall of the top core and the bottom wall of the bottom core.

36. A system according to claim 31, wherein the extraction region is located between the bottom wall of the bottom core and a bottom of the outer body, the extraction tube extending into the extraction region.

37. A system according to claim 31, wherein the proximally extending wall prevents separated wash solution and supernatant from entering the extraction region.

38. A system according to claim 22, wherein the washed red blood cell pump is configured to draw washed red blood cells from the blood component separation device.

39. A system according to claim 22, wherein the first flow rate is between 10 and 30 milliliters per minute.

40. A system according to claim 22, wherein the second flow rate is between 20 and 150 milliliters per minute.

41. A system according to claim 22, wherein a ratio of the first flow rate to the second flow rate is between 1:2 and 1:5.

* * * * *